United States Patent

Berberich

[11] Patent Number: 5,861,758
[45] Date of Patent: Jan. 19, 1999

[54] PROCESS AND SYSTEM FOR THE OPERATION OF A RESISTIVE MOISTURE SENSOR

[75] Inventor: Reinhold Berberich, Frankfurt, Germany

[73] Assignee: VDO Adolf Schindling AG, Frankfurt, Germany

[21] Appl. No.: 902,642

[22] Filed: Jul. 30, 1997

Related U.S. Application Data

[63] Continuation of Ser. No. 611,873, Mar. 5, 1996, abandoned.

[30] Foreign Application Priority Data

Mar. 7, 1995 [DE] Germany ............ 195 07 884.5
Jan. 4, 1996 [DE] Germany ............ 196 00 108.0

[51] Int. Cl.⁶ ............ G01W 1/14; G01N 27/10
[52] U.S. Cl. ............ 324/694; 324/685; 324/676; 324/710; 318/483; 318/DIG. 2
[58] Field of Search ............ 318/483, DIG. 2; 324/689, 676, 677, 678, 711, 694, 710

[56] References Cited

U.S. PATENT DOCUMENTS

| | | | |
|---|---|---|---|
| 4,827,198 | 5/1989 | Mueller | 318/483 |
| 5,140,234 | 8/1992 | Wallrafen | 318/264 |
| 5,200,676 | 4/1993 | Mueller | 318/444 |
| 5,306,992 | 4/1994 | Droge | 318/483 |

FOREIGN PATENT DOCUMENTS 3803138  8/1989  Germany.

*Primary Examiner*—Josie Ballato
*Assistant Examiner*—Jose M. Solis
*Attorney, Agent, or Firm*—Martin A. Farber

[57] ABSTRACT

A process and a system for the operation of a resistive moisture sensor, in particular on the windshield of a motor vehicle, wherein the conductivity of the moisture sensor is measured shortly after a sudden change in a signal fed to the moisture sensor and measured at at least one later time. Information as to the nature and degree of the dirtying of the windshield is obtained by the measured values.

16 Claims, 3 Drawing Sheets

PROCESS AND SYSTEM FOR THE OPERATION OF A RESISTIVE MOISTURE SENSOR

RELATED APPLICATION

This application is a continuation of my application Ser. No. 08/611,873 filed Mar. 5, 1996 now abandoned.

FIELD AND BACKGROUND OF THE INVENTION

The present invention relates to a process and to a system for operating a resistive moisture sensor.

Such a process as well as the system are known from Federal Republic of Germany 38 03 138A1. Resistive moisture sensors are used for instance in order to indicate the presence of moisture or raindrops on the windshield of motor vehicles in order to control the windshield wiper automatically or semiautomatically. For this purpose, conductive paths are applied to the windshield or some other suitable place so that the resistance between the conductive paths decreases with the amount of moisture present.

Whether a wiping or washing of the windshield is necessary depends not only on the amount of moisture but also on the composition of the coating or wetness on the windshield.

SUMMARY OF THE INVENTION

It is an object of the present invention to permit a measurement of the moisture on the windshield which is differentiated with respect to the coating composition.

According to the invention, shortly after a sudden change in a signal fed to the moisture sensor, and at at least one later time, the conductivity of the moisture sensor is measured and information as to the nature and degree of the dirtying of the windshield is provided by the values measured.

The process of the invention makes it possible to distinguish between a new wetting of the windshield with clean water and a wetting with dirty water or water which contains salt which has been thrown up for instance by a car traveling in front, or which for instance results from evaporation of impinging drops having a low content of salt. Furthermore, it is possible to distinguish between large drops of clean water and smaller drops consisting of dirty water or salt water.

In one advantageous embodiment of the process of the invention, the measured values are fed as input values to a table in which are entered output values which are used to control a windshield cleaning system. In this way, advantageous control of a windshield cleaning system as a function of the nature of the dirtying of the windshield is possible.

Although as part of the process of the invention, the conductivity of the moisture sensor can in itself be measured after a sudden change in voltage as many times as desired, it has been found favorable that a first measurement value be obtained shortly after a sudden change in this signal. A second measurement value is obtained at a later time. A switch signal for the windshield cleaning system is derived by comparison of the second measured value with a threshold value. The threshold value is dependent on the first measured value and preferably on a difference between the first measured value and the second measured value. In this connection, the first measured value can possibly be delayed with respect to the sudden change in signal to such an extent that the influence of feed cables and the influence of capacitors for the prevention of voltage peaks are eliminated.

In one advantageous embodiment of the process of the invention, the electric signal fed to the moisture sensor is formed of square voltage pulses. The measured values are obtained by measurement of the current through the moisture sensor when voltage is applied. In this embodiment, there is a sensitivity of the moisture sensor which is substantially independent of the degree of wetting. If it is measured, for instance, that all drops impinging on the moisture sensor have approximately the same conductance, then all drops—from the first up to, for instance, the 10th or 20th—also result in approximately the same change in signal. Depending on the case of use, a measurement of the voltage drop over the sensor through which current passes is also possible within the invention.

Another requirement made on moisture sensors is that electrolytic erosion of the conductive paths and corrosion of parts of the body of a car are avoided. This achieved in a further feature of this embodiment in an advantageous manner wherein positive and negative voltage pulses are fed alternately.

Although the time established for the measurement after, in each case one sudden change, is relatively short, sudden changes in the sensor signal during this time cannot be excluded. Thus, for instance, during this time, a rain drop may impinge on the moisture sensor resulting in the conductivity suddenly increasing. The conductivity can, however, also decrease suddenly upon removal of a rain drop or as a result of a wiping. In order to avoid erroneous measurements as a result of this, it is provided, in a further development of the process of the invention, that in the event of a non-continuous course of the measured sensor signal which takes place within a predetermined time after the sudden change, the information as to the nature and degree of the dirtying are continued to be used instead of the values measured.

Should sudden changes in the signal take place even during several measurement times, the last valid information as to the nature and degree of the dirtying is again employed in each case. Upon the first valid measurement after this, however, information as to the nature and degree of the dirtying which is again valid can be obtained for the control of the wiper by means of the updated measured values.

In one advantageous embodiment of this further development, more than two measurement values are received within the predetermined time. Then it is checked whether the succession in time of the measured values and the succession in time of the differences between the measured values are monotonic. If so, the corresponding measured values are used. If not so, then the information from the measured values after a previous sudden change are used.

In this connection, it is preferably provided that, upon the testing for monotonism, effects of quantification errors and superimposed noise signals be disregarded.

In one advantageous system for the carrying out of the process of the invention for a measurement of the current, a measurement resistor (14) is connected in series with the moisture sensor (1). The voltage drop over the measurement resistor (14) is fed via an amplifier (16) to an analog signal input (9) of a microcomputer (6). A program for the detecting of both measured values, for the correcting of the threshold-value comparison and for the threshold-value comparison is provided in the microcomputer.

However it is also possible to develop a system for carrying out the process of the invention such that the signal is fed in the form of current pulses to the moisture sensor.

The measurement values are obtained from the voltage drop over the moisture sensor, and the voltage drop over the moisture sensor is fed via an amplifier to an analog signal input of a microcomputer.

The invention permits of numerous embodiments.

BRIEF DESCRIPTION OF THE DRAWINGS

With the above and other objects and advantages in view, the present invention will become more clearly understood in connection with the detailed description of a preferred embodiment, when considered with the accompanying drawings, of which.

DETAILED DESCRIPTION OF THE PREFERRED EMBODIMENT

Figure 1:
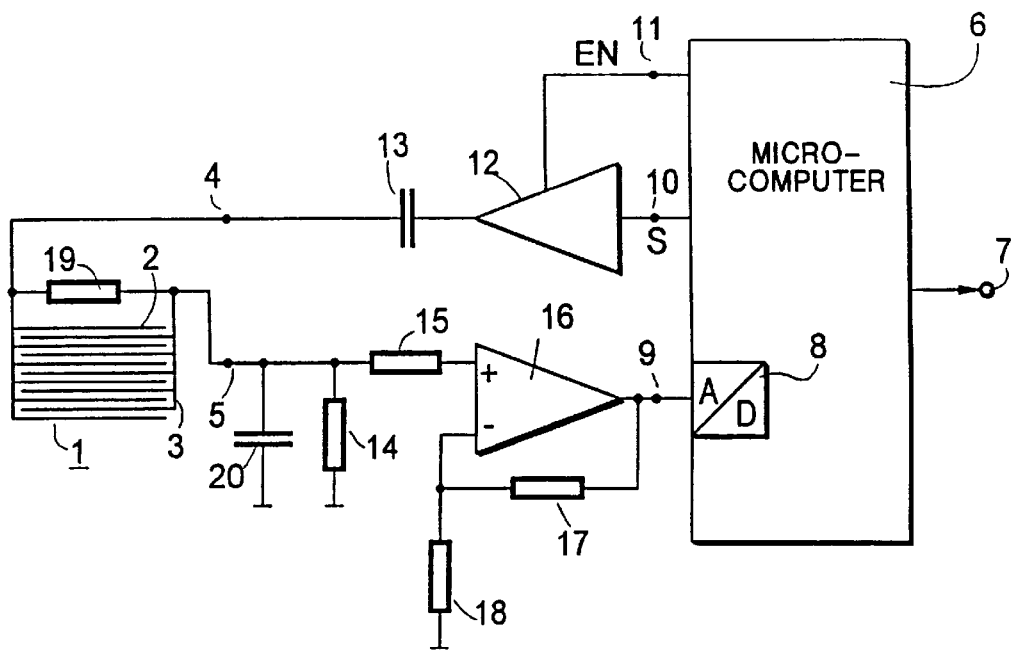
FIG. 1 is a block diagram of a system in accordance with the invention.

In FIG. 1, the moisture sensor 1 comprises conductive paths which form two electrodes 2, 3 which are intermeshed with each other and are connected via terminals 4, 5 with an evaluation circuit. The evaluation circuit comprises a microcomputer 6 having an output 7 from which a signal which characterizes the moisture is obtained. In addition to other elements, the microcomputer 6 includes an analog-to-digital converter 8 having an analog signal input 9. Signals are obtained from outputs 10, 11 of the microcomputer 6. For the application of a pulse-like voltage to the moisture sensor 1, there is provided a switchable amplifier 12, the output of which can be switched to high resistance via a signal EN at a control input. The control input signal EN is received from the output 11 of the microcomputer 6, while the signal input of the amplifier 12 is connected to the output 10 which conducts a signal B. The output of the switchable amplifier 12 is connected via a capacitor 13 to the connection 4 of the moisture sensor 1.

For the measurement of the current through the moisture sensor, the terminal 5 is connected to ground potential via a measurement resistor 14. A capacitor 20 serves for the leading away of voltage peaks. The voltage at the terminal 5 therefore corresponds to the current-proportional voltage drop over the measurement resistor 14 and is fed, via a resistor 15, to the non-inverting input of a difference amplifier 16. Via a voltage divider comprising resistors 17, 18, the inverting input of amplifier 16 receives a part of the output voltage of the difference amplifier 16. The degree of amplification is thus established by the division ratio. The output voltage of the difference amplifier 16 is fed to the analog signal input 9 of the microcomputer 6.

Figure 2A:
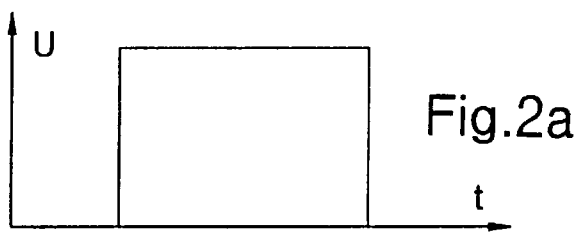
FIGS. 2a, 2b, and 2c show time graphs which serve to explain the dependence of the current through the moisture sensor on the dirtying.
Figure 2B:
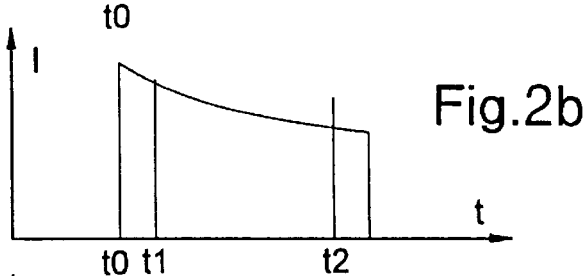
Figure 2C:
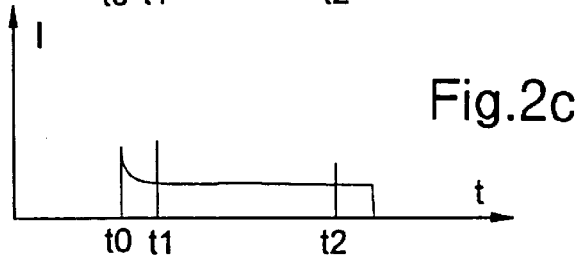

FIG. 2a shows the course of a rectangular voltage U applied to the moisture sensor 1, FIG. 2b shows the course of the voltage on the measurement resistor 14 and therefore also of the current I through the moisture sensor in case of wetting by salt water; and FIG. 2c shows the current of FIG. 2b in the case of wetting with distilled water in a test without the capacitor 20 (FIG. 1). The absolute value of the measured values at t1 and t2 is greatly dependent on the amount of moisture applied and the number of drops. The difference between the measured values is, however, caused by the salt content or ion concentration.

At the time t0, a sudden change in voltage takes place, while at the time t1 a first measurement M1 takes place. The delay between t1 and t0 is intended, as well as the capacitor 20 (FIG. 1), to avoid having the measurements affected by voltage peaks. Shortly before the end of the square pulse, a further measurement M2 of the current I is effected at the time t2. A comparison of FIGS. 2b and 2c shows that at the time t1 the conductivity is considerably greater in the case of wetting with salt water than upon wetting with distilled water and that, in the case of the latter, the conductance at t2 corresponds approximately to the conductance at t1.

Figure 3:
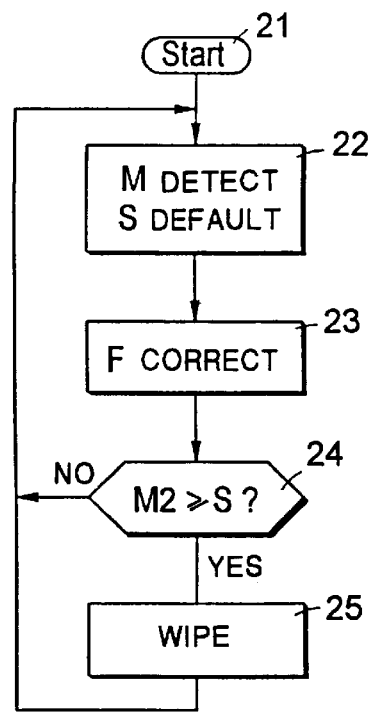
FIG. 3 is a flowchart of a program present in a microcomputer in a system for carrying out the process of the invention.

The program shown in FIG. 3 is started at 21 and continues at 22 with the detection of the measured values M1 and M2 as well as a default threshold value S. In a program part 23 a measurement adjustment factor F from a table is determined as a function of M2 and of the difference between the measured values M1 and M2, and the threshold value S is corrected with the use of the factor F.

At 24 the measured value M2 is then compared with the corrected threshold value S. If M2 is smaller than S, then the program is repeated at 22. However, if M2 reaches or exceeds the value of S, then a wiping process is commenced at 25 and the program is then repeated at 22.

Figure 4:
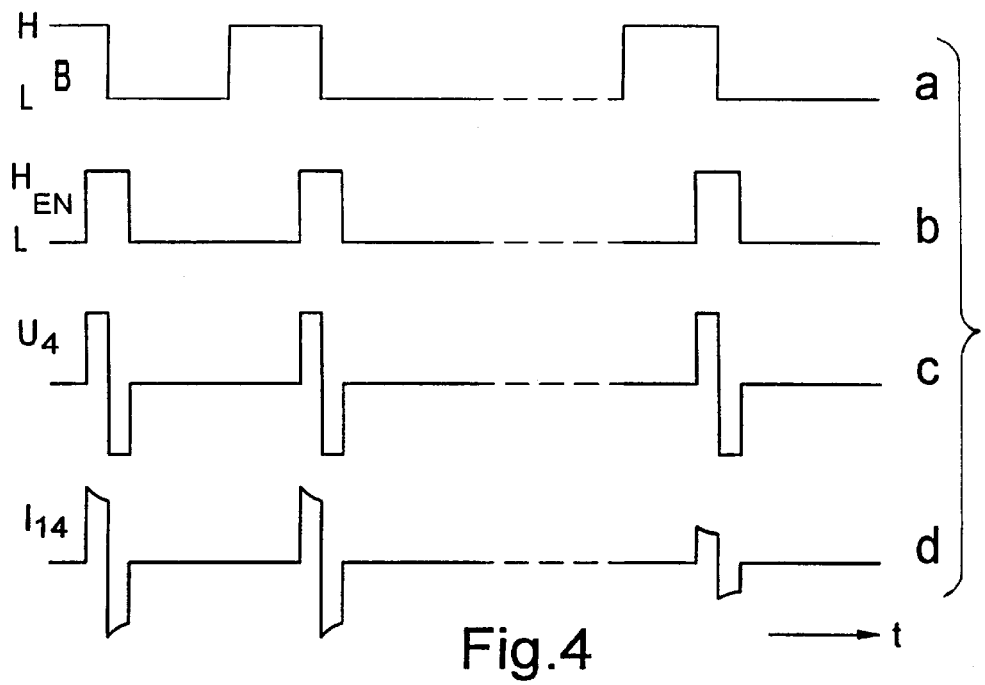
FIG. 4 shows time graphs of different signals occurring in a system constructed in accordance with FIG. 1.

FIG. 4 shows the course of the signals S and EN, of the voltage $U_4$ at the terminal 4, and of the current $I_{14}$ through the measurement resistor 14. For the duration of the pair of pulses shown in lines c and d, the switchable amplifier 12 is turned on by the signal EN (line b) so that during this time the signal B (line a) passes, via the capacitor 13, to the terminal 4. The direct voltage component is suppressed by the capacitor 13, so that a voltage change which is present in each case between the pulses of different polarity results. During the interval between the pairs of pulses, the switchable amplifier 12 is at high resistance so that the voltage (line c) remains initially at 0 even if the signal B increases from L to H. Only when the signal EN again assumes the value H does the positive level arrive as positive flank of the next pair of pulses at the terminal 4.

Fundamentally, the moisture sensor 1 has a conductivity which increases with the amount of moisture so that the current $I_{14}$ also becomes greater with an increase in the amount of moisture. This is indicated in FIG. 4 in the manner that, to the left of the interruption, there are two pairs of pulses of the current $I_{14}$ in the event of a large amount of moisture and, to the right of the interruption, there is one pair of pulses in the event of a smaller amount of moisture.

Figure 5:
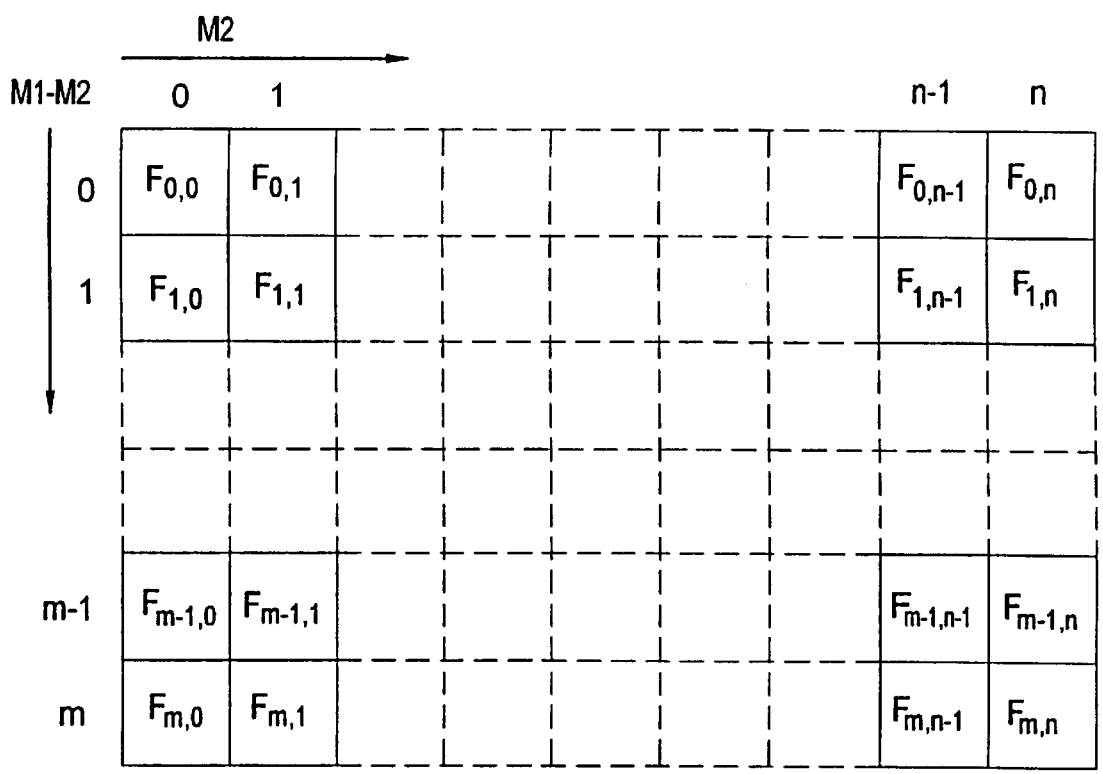
FIG. 5 is a diagrammatic showing of a table with correction values which are processed in the program of FIG. 3.

FIG. 5 serves to explain a table which is stored in the microcomputer 6 (FIG. 1) in which table the factor F is stored in each case for a pair of values M2 and (M1–M2). The factors F can be determined empirically by trial runs. The corrected threshold value S is obtained in simple fashion by multiplication of a previously determined trigger difference by the factor F. With the inclusion of other system values such as, for instance, the drying-time constants of the sensor signal since the last wiping, correction fields are obtained which permit an even more accurate adaptation of the trigger difference to the actual condition of the rain.

Figure 6A:
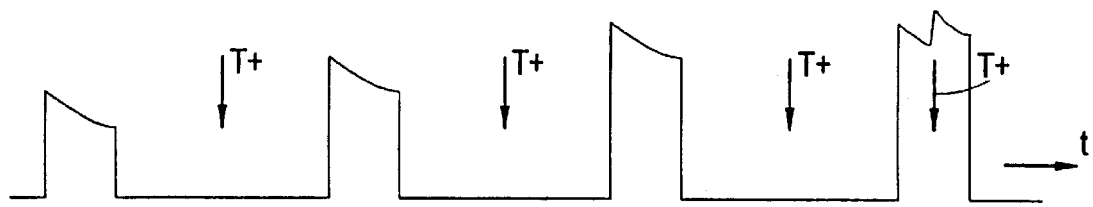
FIGS. 6a and 6b show time graphs of sensor signals having changes in amplitude within a pulse.
Figure 6B:
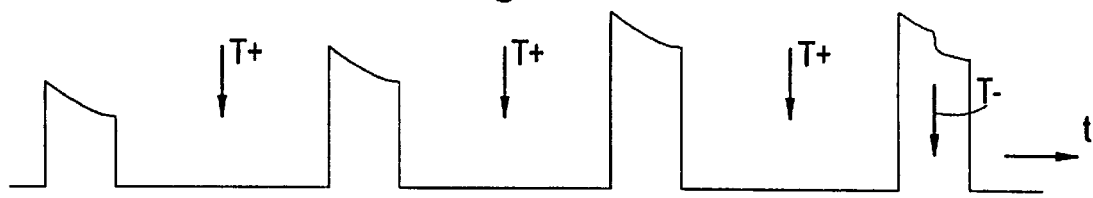

FIGS. 6a and 6b show the course of the signal at terminal 5 in the event that drops fall on the moisture sensor between the individual pulses, as is indicated by arrow T+. If the drops fall between the pulses on the moisture sensor, then the conductivity increases from pulse to pulses, as is shown in idealized form in FIGS. 6a and 6b, in which connection, once again, only the positive pulses are considered. The amplitude of the measurement pulses becomes in this connection larger while the basic course of the signal, however, does not change during the measurement pulses. In the showing of FIG. 6a, a drop now falls on the moisture sensor during the last measurement pulse shown. As a result, the signal is increased suddenly.

Figure 7:
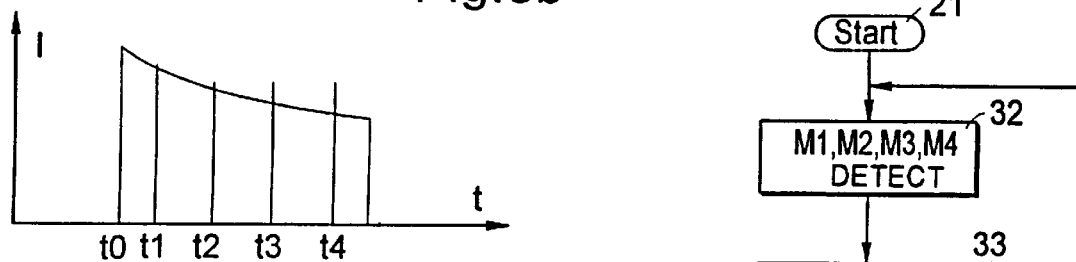
FIG. 7 is a time graph for the formation of four measurement values.

In the showing of FIG. 6b, a drop present on the moisture sensor is removed during a pulse (T–). By these sudden changes, a comparison of two measured values, as has been described in connection with FIG. 2, gives a wrong result. In order to recognize the occurrence of such a change in the signal, it is provided that several measured values be determined, for instance four measured values M1 to M4 at the times t1 to t4, in accordance with FIG. 7.

Figure 8:
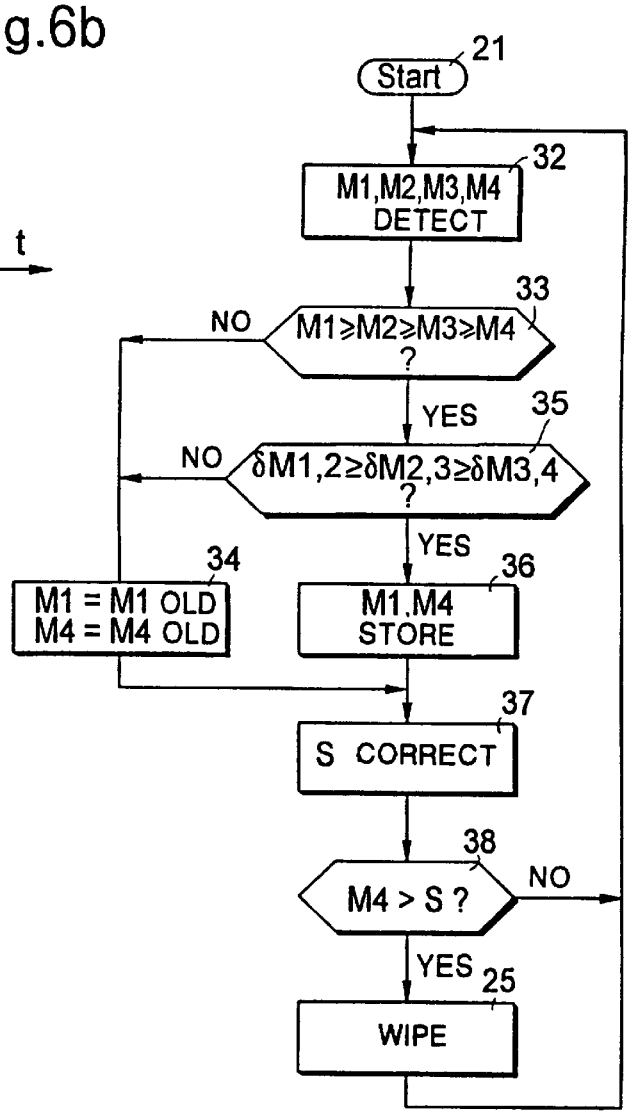
FIG. 8 is a flowchart of another program present in a microcomputer in a system for carrying out the process of the invention.

An evaluation of these measured values is possible with the program shown in FIG. 8, which can take place of the program shown in FIG. 3. After the start at 21, the measured values M1 to M4 are detected at 32. At 38 it is then checked whether the measured values are either the same or represent a monotonally descending sequence. If the condition M1≧M2≧M3≧M4 is not satisfied, then the measured values M1 and M4 are set, at 34, equal to the values from the last valid measurement. However, if the condition is satisfied, then it is checked at 35 whether the differences between the measured values M1 to M4 decrease monotonally. This is the case when the condition δM1,2≧δM2,3≧δM3,4 is satisfied. Then the new measurement values M1 and M4 are stored at 36.

Otherwise, the old measured values are read out from the memory at 34.

At 37, S is corrected with the measured values M1 and M4, as described in connection with FIG. 3. There then takes place a branching 38 upon which it is tested whether the condition M4≧S is satisfied. If so, then a wiping process 25 is brought about as in the case of the program shown in FIG. 3. If the condition at 38 is not satisfied, then operation reverts to 32.

I claim:

1. A method for operating a resistive moisture sensor on a subject to be cleaned of material on the subject, suitable for operating a moisture sensor on a windshield of a motor vehicle, comprising the steps of:

measuring the conductivity of the moisture sensor shortly after a sudden change in a signal fed to the moisture sensor;

repeating said measuring step at least once;

extracting information as to the conductivity and amount of the material on the subject from values measured in each of said measuring steps;

comparing a measurement of said measuring step with a threshold to output a drive signal, suitable for activating a windshield wiper; and adjusting a value of the threshold based on said information.

2. The method according to claim 1, further comprising steps of:

providing a table of values of measurement adjustment factors;

addressing the table with the measured values as input values to the table;

outputting from the table output values corresponding to input addresses; and employing the output values to control a windshield cleaning system.

3. The method according to claim 1, wherein a first measurement value of said first measuring step is obtained shortly after the sudden change in said signal, and a second measurement value of said second measuring step is obtained at a later time;

wherein said method further comprises steps of:

deriving a value of said threshold dependent on one of said measured values and on a difference between the first measured value and the second measured value; and comparing the second measured value with the threshold value to obtain a switch signal for a windshield cleaning system.

4. The method according to claim 1, further comprising steps of:

applying to the moisture sensor an electric signal formed of square voltage pulses; and wherein each of said measuring steps includes a step of measuring a current through the moisture sensor upon application of said voltage pulses for obtaining said measured values.

5. The method according to claim 4, wherein said voltage pulses include positive and negative voltage pulses which are fed alternately in said step of applying the electric signal.

6. The method according to claim 5, wherein, in the event of a non-continuous course of measured sensor signal occurring within a predetermined time after the sudden change, there is a step of employing information as to the conductivity and amount of the material instead of new values of measurement.

7. The method according to claim 6, wherein, upon receipt of more than two measurement values within a predetermined time, there are steps of:

checking whether a succession of measured values and a corresponding succession of differences between the measured values are monotonic; and alternate steps of, in the case of an affirmative result of said checking, employing the corresponding measured values and, in the case of a negative result of said checking, employing information from measured values obtained after a previous sudden change in the signal fed to the moisture sensor.

8. The method according to claim 7, wherein upon said checking for monotonism, there is a step disregarding effects of quantification errors and superimposed noise signals.

9. A system for operating a resistive moisture sensor on a subject to be cleaned, suitable for operation on a windshield of a motor vehicle, the system providing for application of a pulsed electric signal to the sensor wherein pulses provide for sudden changes in the electric signal, the system providing for repetitive measurements of the conductivity of the moisture sensor shortly after such sudden change of signal, the system providing also for an extraction of data from the repetitive measurements as to the nature and degree of a dirtying of the subject; wherein the system comprises:

a current measurement resistor connected in series with the moisture sensor;

a computer having an analog-to-digital converter for receiving an analog signal;

means controlled by the computer for applying a voltage across the series combination of sensor and current measurement resistor resulting in a voltage drop across the measurement resistor; and an amplifier for feeding the voltage drop as the analog signal to an analog input port of said converter;

wherein the computer is operated by a program to detect said measurements, to establish a threshold, and to compare said measurements with the threshold.

10. The system according to claim 9, wherein the pulsed electric signal is fed in the form of current pulses to the moisture sensor, and values of the measurements are obtained from the voltage drop over the moisture sensor.

11. A method for operating a resistive moisture sensor on a subject to be cleaned of material on the subject, suitable for operating a moisture sensor on a windshield of a motor vehicle, comprising the steps of:

applying a measurement pulse comprising a voltage pulse of predetermined duration repetitively across terminals of the sensor;

measuring the conductivity of the moisture sensor at at least two successive measurement times within said pulse duration to obtain a first conductivity measurement and a second conductivity measurement in a sequence of measurement times providing at least two measurements of a sequence of measurements;

establishing a threshold based on a value of one of said measurements and on a difference between at least one pair of measurements in said sequence of measurements;

adjusting a value of the threshold based on subsequent values of said measurements; and verifying that a last measurement of said measurement sequence exceeds said threshold; and wherein a verification that said last measurement of said measurement sequence exceeds said threshold is indicative of a presence of sufficient moisture on the subject to warrant a wiping of the moisture.

12. The method according to claim 11 wherein there are at least three of said measurements in said measurement sequence, and said threshold establishing step further comprises steps of:

comparing successive ones of said measurements to ascertain the presence of a condition wherein their amplitudes decrease monotonically, and that differences between successive pairs of the measurements decrease monotonically; and determining an adjustment factor, upon the presence of said condition, for updating a value of said threshold, and retaining a previous value of said threshold in the absence of said condition;

wherein said condition serves for extracting information as to the conductivity and amount of the material on the subject from values measured in each of said measuring steps.

13. The method according to claim 12, further comprising steps of:

upon attaining a sequence of adjustment factors from measurements in successive ones of said voltage pulses, providing a table of values of the adjustment factors;

addressing the table with values of conductivity measurements as input values to the table;

outputting from the table output values of adjustment factors corresponding to input addresses; and scaling a threshold with an adjustment factor to update a value of the threshold.

14. The method according to claim 13, further comprising a step of employing the output values of the table to control a windshield cleaning system.

15. A method of operating a resistor moisture sensor on a subject to be wiped, the method being suitable for operating a resistive moisture sensor on the windshield of a motor vehicle, the method comprising steps of:

feeding an electric pulsed signal to the sensor;

performing a first measurement and a second measurement of conductivity of the sensor during a pulse of the signal, the second measurement following the first measurement;

comparing one of said measurements with a threshold to obtain a comparison;

outputting a drive signal based on a value of said comparison, said drive signal being suitable for actuation of a windshield cleaning system;

establishing a relation of threshold adjustment factor based on one of said measurements and a difference between said first and said second measurements; and adjusting a value of said threshold by use of said adjustment factor.

16. A method according to claim 14, wherein said one of said measurements is said second measurement.

* * * * *